United States Patent [19]

Higo et al.

[11] Patent Number: 4,810,659

[45] Date of Patent: Mar. 7, 1989

[54] PROCESS FOR INJECTING A MINUTE VOLUME OF A SOLUTION AND AN APPARATUS THEREFOR

[75] Inventors: Yuji Higo, Aichi; Hidechika Hayashi, Kanagawa; Shuji Iwasaki, Tokyo, all of Japan

[73] Assignee: Toyo Soda Manufacturing Co., Ltd., Shinnanyo, Japan

[21] Appl. No.: 918,726

[22] Filed: Oct. 14, 1986

[30] Foreign Application Priority Data

Oct. 15, 1985 [JP]  Japan ................................. 60-229699
Jul. 4, 1986 [JP]  Japan ................................. 61-157608

[51] Int. Cl.[4] ............................................. G01N 1/14
[52] U.S. Cl. ....................................... 436/180; 422/82; 422/100; 222/309; 222/319; 222/335; 222/373; 222/209; 222/378; 222/399; 222/400.5
[58] Field of Search ................. 436/180; 422/100, 82; 222/399, 400.5, 373, 378, 309, 319, 335, 209, 633; 251/186, 325, 155; 137/14, 147, 169

[56] References Cited

U.S. PATENT DOCUMENTS

| | | | |
|---|---|---|---|
| 3,672,545 | 6/1972 | Marand | 222/400.5 X |
| 3,795,349 | 3/1974 | Schetinin et al. | 222/400.5 X |
| 3,832,135 | 8/1974 | Drozdowski et al. | 436/49 X |
| 4,088,446 | 5/1978 | Huber et al. | 134/105 |

Primary Examiner—Barry S. Richman
Assistant Examiner—Lynn M. Kummert
Attorney, Agent, or Firm—Oblon, Fisher, Spivak, McClelland & Maier

[57] ABSTRACT

Process for injecting a minute volume of a solution from a nozzle device by positive pressure applied from a source of compressed air with or without positive pressure applied in parallel from a cylinder device, comprising applying the positive pressure from the compressed air source at least in a final period of injection. The process enables in injecting minute volumes of solution to remarkably decrease the injection error due to a small fraction of solution remaining at the lower end of the nozzle and can be applied to advantage to those apparatus for analyses and measurements which strictly require precision in injection.

4 Claims, 4 Drawing Sheets

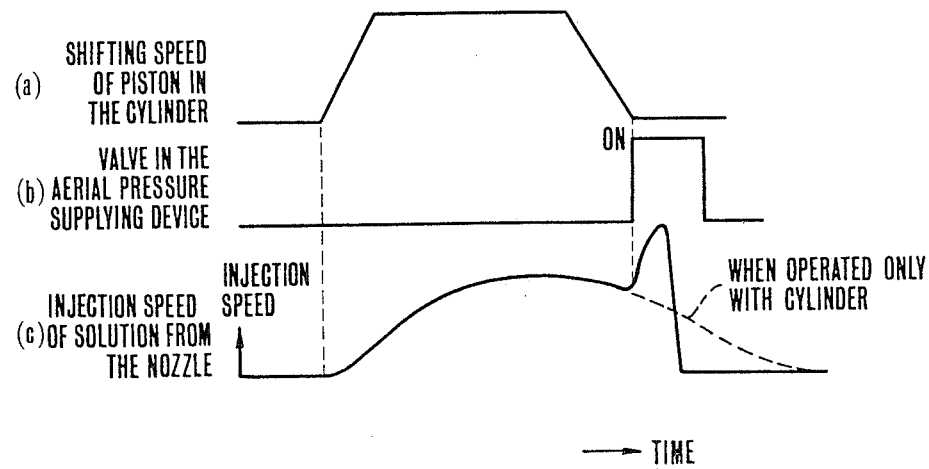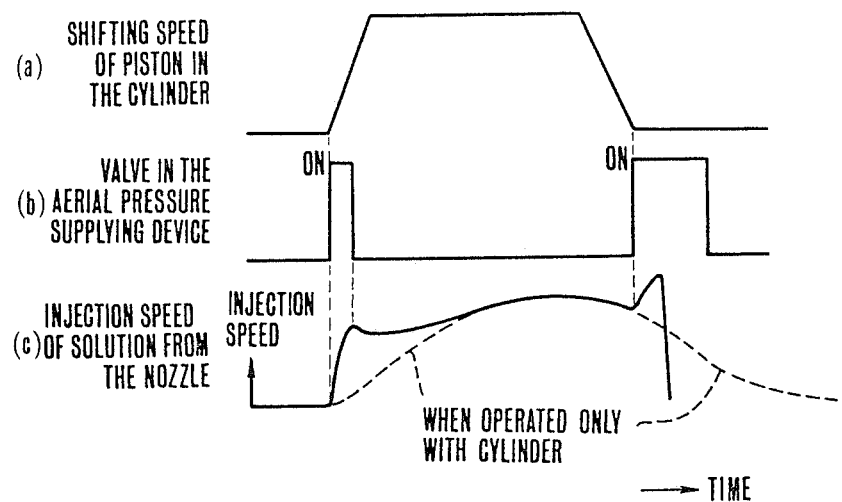

4,810,659

PROCESS FOR INJECTING A MINUTE VOLUME OF A SOLUTION AND AN APPARATUS THEREFOR

BACKGROUND OF THE INVENTION

1. Field of the Invention

The present invention relates to a process and an apparatus therefor for taking a minute volume of a solution from a reservoir and injecting the solution into a vessel with high precision.

2. Description of the Prior Art

An injection apparatus for delivering minute volumes each ranging from several $\mu l$ to several hundred $\mu l$ of a sample solution is generally used in biochemical immunoassay (IA) and liquid chromatography.

Previous injection apparatuses are usually provided with a cylinder device connected to the cavity of a nozzle device into which an object solution is sucked. The solution is sucked by the backward motion of a piston of the cylinder device and injected into a vessel by the forward motion of the piston. However, when this kind of an injection apparatus is used to inject minute volumes of a solution as mentioned above, significant errors of injection have often occurred.

Provided that the lower end of the nozzle in an inverted conical shape has a diameter of about 0.3–0.5 mm and the tube wall is about 0.3–0.5 mm thick, an injection error of several $\mu l$ is inevitable when about 200 $\mu l$ of a solution is sucked and injected by the forward and backward motion of a piston in the cylinder device. The error is not negligibly small when a high injection precision is required. The error of course becomes more remarkable when a minute volume such as several $\mu l$ to several ten $\mu l$ is concerned.

SUMMARY OF THE INVENTION

The present invention has been made to overcome above-mentioned problems and intends as its object to provide a process for injecting a minute volume of solution with a far improved injection precision and an apparatus for injection suitable to conducting the process.

Another object of this invention is to provide a process and an apparatus therefor which may be suitably employed in bioassay systems to pipet and deliver sample solutions.

The present invention carries out the above-mentioned objects by a process of injection in which a solution sucked in the nozzle device is injected by the positive pressure applied from a source of compressed air (hereinafter designated as air pressure applying operation) together with the positive pressure applied in parallel from the cylinder device (hereinafter designated as cylinder operation), where the air pressure applying operation (in parallel with the cylinder operation) is used at least in the final period of injection.

The injection apparatus suitably used for the process comprises a nozzle device to suck and inject a solution, a variable volume cylinder device connected to the cavity of the nozzle, a compressed air source connected to the cavity of the nozzle to apply positive pressure for injecting the solution, and a valve device which is placed on a line connecting from the compressed air source to the nozzle and is opened either momentarily or continuously for the injection of the solution.

DETAILED DESCRIPTION OF THE INVENTION

According to the inventors' investigation, the above mentioned injection error comes about due to the loss of the object solution to be delivered. Particularly, a part of the solution flows around to the outer wall of the nozzle or remains on the inner wall of the nozzle and is left there undelivered. This probably has occurred mainly because the speed of injection is lower in the final (also in the initial) period of injection than in the midway of injection, if the injection results from the positive pressure applied from the cylinder device.

This phenomenon becomes remarkable when a sample solution wets the nozzle material as solutions of biological samples do and also when the piston of the cylinder device is driven by the screw-driven mechanism using a pulse motor for delivering minute volumes. This is explained, for example, by referring to FIGS. 6(a), (b) and 7(a), (b). FIG. 6(a) shows the speed of piston when the cylinder device is driven in the rectangular mode with a pulse motor, while FIG. 7(a) shows speed in the trapezoid mode with a pulse motor. The speed of injection from the nozzle, as shown in FIG. 6(b) and FIG. 7(b), forms a gradual slope in the final (also in the initial) period of injection.

In this connection, the present invention includes an air pressure applying operation in injecting a solution from the nozzle for the purpose of minimizing the volume of the solution which may remain undelivered at the lower end of the nozzle. The air pressure applying operation is employed at least in the final period of injection, particularly to improve the completeness in adding drops of solution. FIG. 4(a)–(c) illustrate the case when the air pressure applying operation is adopted in the final period of injection and, in FIG. 5(a)–(c), the air pressure applying operation is adopted in both final and initial periods of injection. The two figures demonstrate that a high injection speed can be obtained in the final period of injection.

The cylinder device is preferably employed to suck a solution in the nozzle and may be used in parallel, if there is no objection, for injecting the solution. The air pressure applying operation should be employed in the final period of injection (in parallel to use of the cylinder device, if required). However, in the intermediate period of injection, either the air pressure applying operation or the cylinder operation may be selected for use, or otherwise the two operations may be operated in parallel or alternated. Very high precision injection can be obtained by employing the cylinder operation throughout the whole period of injection and the air pressure applying operation in parallel in the initial and final periods of injection.

In the preferred embodiment of this invention, the valve device is opened only for a short time after the initiation of the cylinder operation in the initial period of injection, to assure rapid growth of the speed with which the solution in the nozzle is delivered. Then the injection of the solution in the nozzle is continued by the cylinder operation and, in the final period, the valve device is opened again to assure the air pressure for rapid delivery of solution and the complete removal of the last drop from the lower tip of the nozzle.

The air pressure applying operation in the final period, as described above, should, preferably, continue in ordinary cases for 0.2–1 sec, more preferably, 0.2–0.5 sec, and the same in the initial period preferably for 0.1-0.2 sec.

The nozzle devices to which the present invention can be applied include vertically movable nozzles as well as stationary nozzles. There is no restriction on the structure of the nozzle device, but the device is generally used with a replaceable nozzle tip attached at the lowest end of the nozzle.

The cylinder device which is connected to the cavity in the nozzle device and is mostly employed for sucking a solution may include those of the mechanical type in which a piston is moved by a screw driven mechanism operated by a pulse motor and those operable by air pressure. A certain amount of a solution is sucked by the backward movement of the piston from the initial position to generate negative pressure in the cylinder connected to the nozzle. The piston is moved to the initial position during or after the injection of solution.

The compressed air source which is connected for the air pressure applying operation to the nozzle device, and the valve device installed en route on the connecting line, are usually formed as an accumulator for the air pressure, a pump or a compressed air tank, and an electromagnetic valve of the ordinarily closed type. Preferably a flow rate adjusting valve is inserted as part of the valve device on the connecting line. On-off state of the valves including the electromagnetic valve may be accomplished by a manual switch, but on an automated apparatus the operation can be performed with the aid of a sequential control circuit which works in synchronization with other devices for the injection.

The air pressure applying operation for injection is conducted for the purpose of applying an air pressure large enough to allow as little solution as possible to remain on the inner and outer surfaces of lower end of the nozzle. The pressure should amount generally to 0.1-5, preferably 0.1-0.5 atmospheres by gauge. Too small an air pressure is not sufficient to eliminate the remaining solution, but on the other hand too large a pressure may cause the solution from the lower end of the nozzle to be spattered.

The air flow rate is adjusted by an air flow adjusting valve to a range of 20 to 100 ml/min, preferably 40 to 60 ml/min.

The time duration in which the valve device is momentarily opened to apply an air pressure may be, at the initial period, selected so as to apply an amount of air sufficient to increase the solution ejection speed up to a prescribed rate in a short time, but not more than the amount of the solution contained in the nozzle. At the final period, the air pressure necessary for the last period of ejection of solution is assured, and thus the amount of remaining solution can be minimized, and an almost constant amount of the solution injection can be assured from the initial period through the final period.

In case the compressed air source employed is of such a kind as to generate a pressure only when required, the valve device may be composed of a check valve (a single direction valve).

The present invention will be described in detail with reference to the accompanying drawings.

BRIEF EXPLANATION OF THE DRAWINGS

FIGS. 4 and 5 illustrate the speed of injection of solution according to this invention, while

DETAILED DESCRIPTION OF THE PREFERRED EMBODIMENTS

Figure 1:
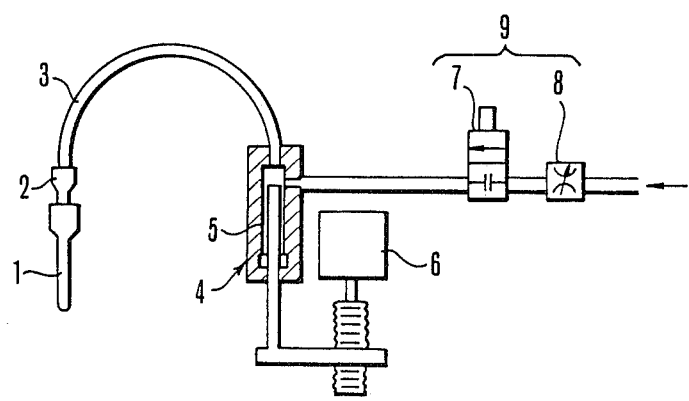
FIG. 1 through FIG. 3 show examples of embodiments of this invention.

In FIG. 1, 1 is a nozzle tip which is replaceable and fitted to a nozzle holder 2, and the replacement is made by a replacing device not shown in the figure. A flow route is provided via the nozzle holder 2 connecting the axial hole in the nozzle tip 1 with an air tube 3.

The air tube 3, at the end opposite that connected to the nozzle holder 2, is branched and one branch is connected to a cylinder volume 5 in a cylinder device 4 which is screw driven by a pulse motor 6, while the other branch is connected to an air pressure accumulator not shown in the figure via a valve device 9 which is composed of an ordinarily closed electromagnetic valve 7 and a flow rate adjusting valve 8. The electromagnetic valve 7 is connected to a control circuit not shown in the figure and is motivated, when required during the injection, to temporarily open the route in synchronization with the operation of other devices.

Operations take place as follows.

At first, the nozzle tip 1 is fitted to the nozzle holder 2 and the lower end is dipped to a certain depth in a sample solution placed in the sample vessel. Under the situation mentioned, the piston in the cylinder device 4 is moved in the pull direction (downwards in the figure) to suck the sample solution in the nozzle tip 1. The amount of sample taken can be controlled with a sufficiently high precision by controlling the distance of movement of the piston. It is also possible in the present embodiment to perform injection of a diluted solution. For this purpose, a quantity of dilution water is first sucked in the nozzle tip, followed by suction of a sample solution.

Subsequently, the nozzle tip is pulled out of the sample vessel with the piston in the cylinder device being fixed and is brought just above a sample injection vessel.

Then the solution in the nozzle tip 1 is transferred by injection into the vessel. This is performed, for example, by moving the piston in the cylinder device in the "insert" direction or to the home position and the electromagnetic valve 7 is momentarily switched to the "open" state at the same time in order to momentarily apply a flow of compressed air at a rate determined by the flow rate adjusting valve 8. When the injection has been finished, the electromagnetic valve 7 is momentarily switched to the "open" state to minimize the amount of solution remaining on the surface of the tip. Thus, a course of injection is completed. The operations may be repeated for a further procedure.

Using the apparatus shown in FIG. 1, injections of a solution from the nozzle tip 1 were performed according to the conditions and procedures described below. The precision of the injection is shown in CV-values in Table 1.

Comparison example

Injection of solution by the cylinder operation alone.

EXAMPLE 1

Injection of solution by the cylinder operation, successively followed by the air pressure applying operation (operation in accordance with FIG. 4).

EXAMPLE 2

Injection of solution by the successive operations of the temporary air pressure applying operation, the cylinder operation and the air pressure applying operation (operation in accordance with FIG. 5).

Diameter of nozzle tip (at the lower end): 0.3 mm
Thickness of wall of nozzle tip: 0.3–0.5 mm
Sample: 8% BSA in Saline
Amount of injection (sucked and injected): See Table 1.
Amount of injection (Sample+Dilution): 200 μl
Operations of injection
  Cylinder operation: 200 μl/2 sec
  Pressure of air: 0.1 atmosphere by gauge
  Duration of pressure application
    Example 1 (final period): 0.5 sec
    Example 2 (initial period): 0.1 sec
    Example 2 (final period): 0.5 sec
  Flow rate adjustment: 10 ml/10 sec

TABLE 1

| Amount of injection (μl) | Comparison example CV (value) | Example 1 CV (value) | Example 2 CV (value) |
| --- | --- | --- | --- |
| 100 | 1.88 | 1.60 | 0.35 |
| 50 | 1.53 | 1.85 | 0.22 |
| 25 | 5.29 | 0.85 | 0.97 |
| 10 | 3.13 | 1.05 | 0.96 |
| 5 | 6.05 | 0.86 | 0.78 |

In the table, $$CV\text{(value)} = \frac{\sqrt{\frac{\Sigma(x_i - x)^2}{n - 1}}}{x} \times 100\%$$

where
n: frequency (10 for each example)
x: mean of $x_i$'s

The result manifests the superiority of the precision in injection as obtained by the present invention to those in the comparison example. This invention can be expected to contribute to those analytical systems in which precision in injection seriously influences analytical results.

Particularly in Example 2 where the pressure application in the initial period of injection accelerates the injection up to a certain speed from the start of the process, the solution to be injected does not flow around to the outer wall of the nozzle. When a viscous solution is involved, the solution flows more slowly in the nozzle. This solution is slowly injected by the pressure of the cylinder and the acceleration by the air pressure in the final period can effect complete injection of solution without leaving a significant trace at the lower end of the nozzle.

Of course, the present invention can be realized in various modified forms not restricted to the embodiment indicated in FIG. 1.

Figure 2:
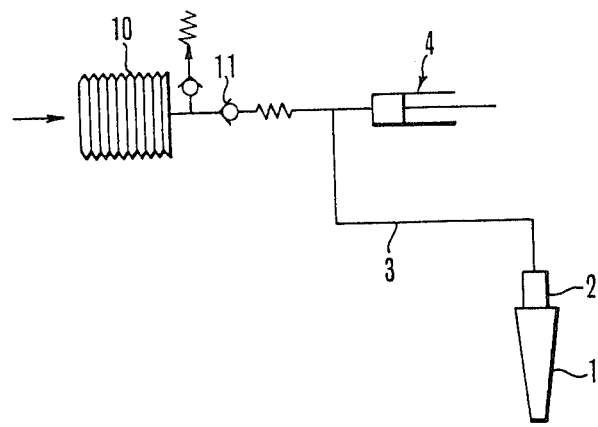

An example in FIG. 2, for instance, employs a bellows type air pump 10 as a compressed air source and a check valve 11 in place of a valve device, other elements being the same as in Example 1.

In case of this example, the air pressure is generated by the mechanical or manual operation of the cylinder device to compress air in the air pump 8 and the pressure is transferred via the check valve 11 to the interior of the nozzle tip. This offers an economical construction of the apparatus because the compressed air source and the valve device can be obtained cheaply. The check valve should have so high a set pressure as not to be opened at the suction of solution may be determined in correlation to the cylinder device.

Figure 3:
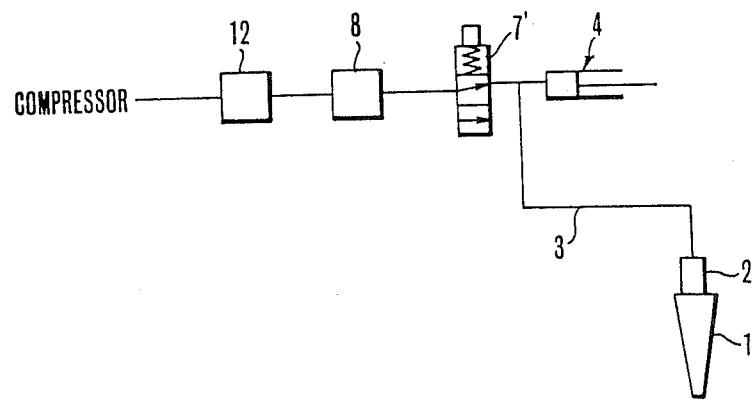
Figure 6:
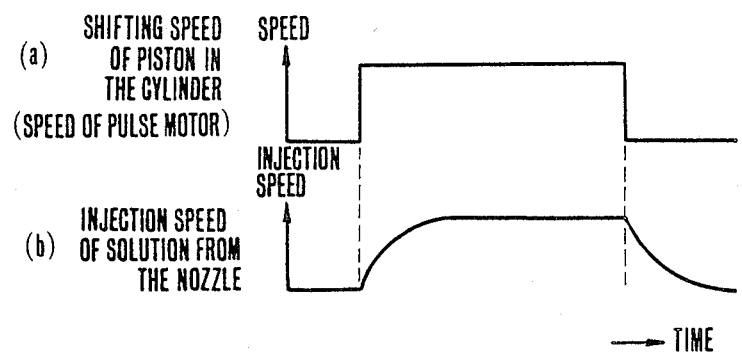
FIGS. 6 and 7 show how the speed of injection varies when the process is carried out with single cylinder operation.
Figure 7:
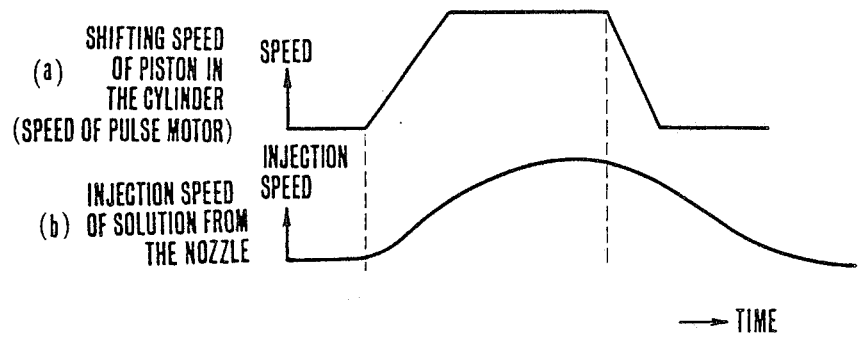

The example shown in FIG. 3 employs a compressor (not shown in the figure) and a pressure regulator 12 as a compressed air source. Other components in the assembly are the same as in FIG. 1 except the electromagnetic valve 7' which is normally open. This example is evaluated to be advantageous because the compressed air from the compressed air source is normally released via the electromagnetic valve 7' into the atmosphere instead of to the cylinder device.

When the injection apparatus of this example is employed in an analytical measurement system, the compressor can be also used for an energy source for other instruments. This permits increased freedom in designing the system and the common use of an apparatus.

As has been described above, the present invention enables in the injecting of minute volumes of solution to remarkably decrease the injection error due to a small fraction of the solution remaining at the lower end of the nozzle and therefore this invention can be applied to advantage to those apparatuses for analyses and measurements which require strict precision in injection.

In case a cylinder device prepared for suction of a solution is used for injection with an intention to realize complete delivery of the last drop of the solution, the stroke of the piston on injection is usually longer than the stroke on suction and therefore there is a void stroke on suction. Nowadays air cylinder devices employ smaller diameters and longer stems for the sake of more precision. The trend may probably give rise to troubles in controlling the amount of suction and adjustment of the injection speed. On the contrary the apparatus of this invention is free from such a trouble and permits a small and precise injection to be realized with a large effect.

What is claimed is:

1. A process for injecting a minute volume of a solution into a vessel with high precision, comprising the steps of:
   providing a reservoir including a nozzle device with a minute volume of a solution to be injected into a vessel;
   using mechanical pressure acting on the volume in a discharge step to discharge the volume from said reservoir and inject the volume into said vessel via said nozzle device; and
   supplementing said discharge step by supplying a flow of pressurized air through said nozzle device during at least a final portion of said discharge step.

2. Process for injecting a minute volume of a solution into a vessel according to claim 1, wherein said pressurized air is supplied in initial and final portions of said discharge step and said mechanical pressure comprises positive pressure from a cylinder device and is applied without intermission through an intermediate period between the initial and final portions of said discharge step.

3. An apparatus for injecting a minute volume of a solution into a vessel with high precision, comprising:
   a nozzle device;
   a variable volume cylinder means fluidically connected to said nozzle device for filling and discharging a solution into and from said nozzle device respectively; and means for supplementing said cylinder means during discharging of the solution, said supplementing means comprising means for selectively supplying a flow of compressed air through said nozzle device.

4. Apparatus for injecting a minute volume of a solution into a vessel according to claim 3, wherein the nozzle device is attached to a replaceable disposable tip.

* * * * *